United States Patent
Ross, Jr. et al.

(10) Patent No.: US 8,993,769 B2
(45) Date of Patent: Mar. 31, 2015

(54) PROCESSES TO PRODUCE CERTAIN 2-(PYRIDINE-3-YL)THIAZOLES

(71) Applicant: Dow AgroSciences LLC, Indianapolis, IN (US)

(72) Inventors: Ronald Ross, Jr., Zionsville, IN (US); Carl DeAmicis, Indianapolis, IN (US); Yuanming Zhu, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 18 days.

(21) Appl. No.: 13/905,183

(22) Filed: May 30, 2013

(65) Prior Publication Data

US 2013/0324735 A1    Dec. 5, 2013

Related U.S. Application Data

(60) Provisional application No. 61/655,076, filed on Jun. 4, 2012.

(51) Int. Cl.
*C07D 417/04* (2006.01)

(52) U.S. Cl.
CPC .................................. *C07D 417/04* (2013.01)
USPC ....................................................... 546/270.4

(58) Field of Classification Search
USPC ....................................................... 546/270.4
See application file for complete search history.

(56) References Cited

U.S. PATENT DOCUMENTS 5,219,824 A    6/1993  Sing et al.
2010/0292253 A1   11/2010  Trullinger et al.

FOREIGN PATENT DOCUMENTS

WO    WO2008090382 A1    7/2008
WO    PCT/US2013/043204 A1    11/2013

OTHER PUBLICATIONS

Dorwald, Side Reactions in Organic Synthesis, 2005, Wiley: VCH Weinheim Preface, pp. 1-15 & Chapter 8, pp. 279-308.*
Thompson, et al. Ugi Reactions with Ammonia Offer Rapid Access to a Wide Range of 5-Aminothiazole and Oxazole Derivatives. J. Org. Chem. 74(18): 7084-7093, 2009.

* cited by examiner

*Primary Examiner* — Patricia L Morris
(74) *Attorney, Agent, or Firm* — Carl D. Corvin

(57) ABSTRACT

The invention disclosed in this document is related to the field of processes to produce certain 2-(pyridine-3-yl)thiazoles as intermediates for the synthesis of pesticidal thiazole amides.

8 Claims, No Drawings

US 8,993,769 B2

PROCESSES TO PRODUCE CERTAIN 2-(PYRIDINE-3-YL)THIAZOLES

CROSS REFERENCES TO RELATED APPLICATIONS

This Application claims priority from, and benefit of, U.S. provisional application 61/655,076 filed on Jun. 4, 2012. The entire content of this provisional application is hereby incorporated by reference into this Application.

FIELD OF THE DISCLOSURE

The invention disclosed in this document is related to the field of processes to produce certain 2-(pyridine-3-yl)thiazoles as intermediates for the synthesis of pesticidal thiazole amides.

BACKGROUND OF THE DISCLOSURE

Controlling pest populations is essential to modem agriculture, food storage, and hygiene. There are more than ten thousand species of pests that cause losses in agriculture. For world-wide agricultural losses amount to billions of U.S. dollars each year. Pests, such as termites, are also known to cause damage to all kinds of private and public structures resulting in billions of U.S. dollars in losses each year. Pests also eat and adulterate stored food, resulting in billions of U.S. dollars in losses each year, as well as deprivation of food needed for people.

Certain pests have or are developing resistance to pesticides in current use. Hundreds of pest species are resistant to one or more pesticides. Accordingly, there exists a continuous need for new pesticides and for processes of forming such pesticides.

WO 2010/129497 (the entire disclosure of which is incorporated herein) discloses certain pesticides. However, the processes of making such pesticides may be both costly and inefficient. Accordingly, there exists a need for processes of efficiently forming such pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"alkynyloxy" means an alkynyl further consisting of a carbon-oxygen single bond, for example, pentynyloxy, hexynyloxy, heptynyloxy, octynyloxy, nonynyloxy, and decynyloxy.

"aryl" means a cyclic, aromatic substituent consisting of hydrogen and carbon, for example, phenyl, naphthyl, and biphenyl.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbomenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbomyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbomyloxy, and bicyclo[2.2.2]octyloxy.

"cyclohaloalkyl" means a monocyclic or polycyclic, saturated substituent consisting of carbon halo, and hydrogen, for example, 1-chlorocyclopropyl, 1-chlorocyclobutyl, and 1-dichlorocyclopentyl.

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoroethyl, 2-fluoroethyl, 2,2,2-trifluoroethyl, chloromethyl, trichloromethyl, and 1,1,2,2-tetrafluoroethyl.

"heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

DETAILED DESCRIPTION OF THE DISCLOSURE

An embodiment of this invention is illustrated in Scheme One

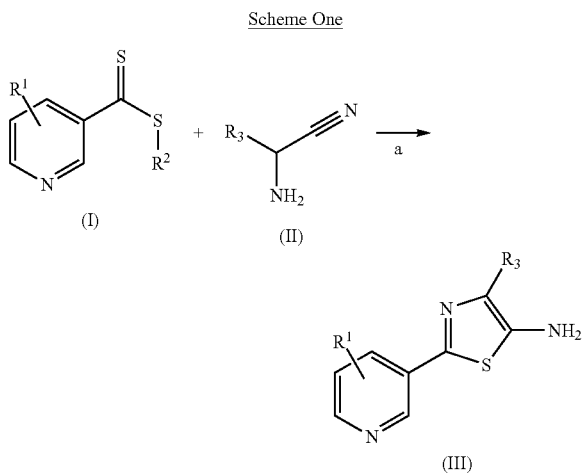

wherein
- (A) each $R^1$ is independently selected from H, F, Cl, Br, I, CN, $NO_2$, and substituted or unsubstituted $(C_1-C_6)$alkyl, wherein each substituted $R^1$ has one or more substituents independently selected from F, Cl, Br, I, CN, $NO_2$, $(C_1-C_6)$alkyl, and $(C_1-C_6)$haloalkyl;
- (B) $R^2$ is selected from substituted or unsubstituted $(C_1-C_6)$alkyl, substituted or unsubstituted $(C_2-C_6)$alkenyl, substituted or unsubstituted $(C_1-C_6)$alkoxy, substituted or unsubstituted $(C_2-C_6)$alkenyloxy, substituted or unsubstituted $(C_3-C_{10})$cycloalkyl, substituted or unsubstituted $(C_3-C_{10})$cycloalkenyl, substituted or unsubstituted $(C_6-C_{20})$aryl, substituted or unsubstituted $(C_1-C_6)$alkyl)$(C_6-C_{20})$aryl, and substituted or unsubstituted $(C_1-C_{20})$heterocyclyl, wherein each substituted $R^2$ has one or more substituents independently selected from F, Cl, Br, I, CN, $NO_2$, $(C_1-C_6)$alkyl, $(C_2-C_6)$alkenyl, $(C_1-C_6)$haloalkyl, $(C_2-C_6)$haloalkenyl, $(C_1-C_6)$haloalkyloxy, $(C_2-C_6)$haloalkenyloxy, $(C_3-C_{10})$cycloalkyl, $(C_3-C_{10})$cycloalkenyl, $(C_3-C_{10})$halocycloalkyl, $(C_3-C_{10})$halocycloalkenyl, $(C_6-C_{20})$aryl, and $(C_1-C_{20})$heterocyclyl; and
- (C) $R^3$ is selected from H, substituted or unsubstituted $(C_1-C_6)$alkyl, substituted or unsubstituted $(C_3-C_{10})$cycloalkyl, substituted or unsubstituted $(C_1-C_6)$alkyl$(C_3-C_{10})$cycloalkyl, substituted or unsubstituted $(C_6-C_{20})$aryl, and substituted or unsubstituted $(C_1-C_6)$alkyl$(C_6-C_{20})$aryl, wherein each substituted $R^3$ has one or more substituents independently selected from F, Cl, Br, and I.

In another embodiment of this invention each $R^1$ is independently selected from H, F, and Cl.

In another embodiment of this invention $R^1$ is H.

In another embodiment of this invention $R^3$ is selected from H, $(C_1-C_6)$alkyl, $(C_1-C_6)$haloalkyl, and $(C_6-C_{20})$aryl.

In another embodiment of this invention $R^3$ is selected from H, $CF_3$, $CH_2F$, $CHF_2$, $CH_3$, $CH_2CH_3$, $CH(CH_3)_2$, and phenyl.

In another embodiment of this invention $R^3$ is selected from H and $CH_3$.

In general, S—$R^2$ is a leaving group wherein $R^2$ is part of the leaving group that does not substantially and adversely affect the desired reaction. It is desirable that $R^2$ is a group that beneficially affects the volatility of the thio by-product of the reaction.

In step a, compounds (I) and (II) are cyclized to produce compound (III). This step is conducted in the presence of a base when compound (II) is in the form of a salt. Suitable bases include, but are not limited to, sodium bicarbonate, potassium bicarbonate, sodium carbonate, cesium carbonate, potassium carbonate, sodium hydroxide, potassium hydroxide, sodium bisulfate, sodium acetate, potassium acetate, ammonium hydroxide, sodium methoxide, potassium methoxide, sodium ethoxide, potassium ethoxide, triethylamine and pyridine. The reaction can be conducted at ambient temperature and pressure, but higher or lower temperatures and pressures can be used, if desired. The reaction is conducted in a polar protic solvent. Examples of such solvents include, but are not limited to, n-butanol, isopropanol, n-propanol, ethanol, methanol, and water. Currently, methanol is preferred.

One advantage of step a over the art is that compound (III) is generally produced as a substantially pure solid that does not need additional purification procedures. Another advantage with these processes is that in compound (III)—if $R^3$ is H, it can be halogenated. Consequently, at this point $R^3$ additionally now includes F, Cl, Br, and I (see Scheme Two). As an additional advantage compound (IV) can be in the form of a salt.

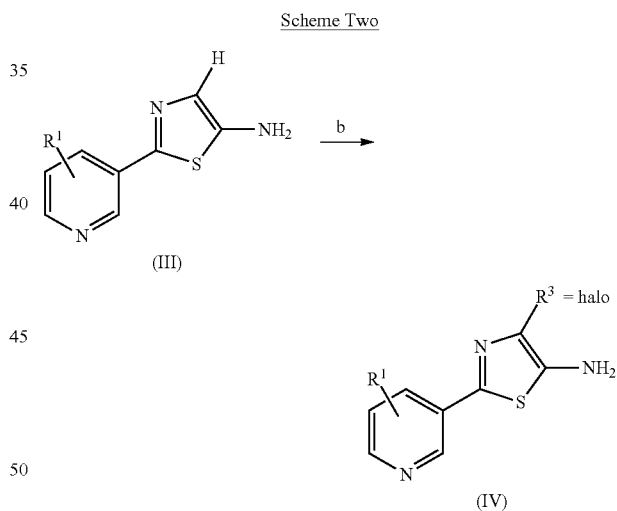

In step b, any halogenating agent can be used, for example, 1-chloropyrrolidine-2,5-dione, N-bromosuccinimide, and 1-chloromethyl-4-fluoro-1,4-diazoniabicyclo[2.2.2]octane bis(tetrafluoroborate). Polar solvents can be used such as dichloromethane, tetrahydrofuran, ethyl acetate, acetone, dimethylformamide, acetonitrile, and dimethyl sulfoxide. Currently, dichloromethane is preferred. The reaction can be conducted at ambient temperature and pressure, but higher or lower temperatures and pressures can be used, if desired. Currently, temperatures from about 0° C. to about ambient are preferred.

In another embodiment of this invention $R^3$ is preferably Cl.

Compound (III) or compound (IV) can be further reacted to form certain pesticides disclosed in WO 2010/129497 (the entire disclosure of which is incorporated herein by reference).

EXAMPLES

The examples are for illustration purposes and are not to be construed as limiting the invention disclosed in this document to only the embodiments disclosed in these examples.

Starting materials, reagents and solvents which were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable to name a molecule, the molecule is named using conventional naming rules. All NMR are in ppm (δ) and were recorded at 300, 400, or 600 MHz unless otherwise stated.

Example 1

Preparation of 2-(pyridin-3-yl)-1,3-thiazol-5-amine

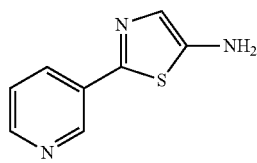 [SMILES: Nc1cnc(-c2cccnc2)s1]

To a dry 500 ml round bottom flask equipped with magnetic stirrer, thermometer, bleach scrubber, and addition funnel was charged 27.6 g (179 mmoles) of aminoacetonitrile bisulfate, and 200 mLs of anhydrous methanol. The solution was cooled to ~0° C. and 24.15 g (239 mmoles) of triethyl amine was added dropwise at a rate that maintained the temperature below 10° C. After 10 minutes, 20.2 g (119 mmoles) of methyl pyridine-3-carbodithioate was added dropwise in 50 mLs of anhydrous methanol. The reaction mixture was stirred at ambient temperature for 20 hours, after which, the solvent was removed under vacuum on a rotary evaporator. The residue was poured into 500 mLs of water and extracted with methylene chloride (4×100 mLs). The combined methylene chloride extracts were washed with 100 mLs of water, 100 mLs of saturated aqueous sodium chloride solution, dried over anhydrous magnesium sulfate, filtered, and concentrated under vacuum on a rotary evaporator. The crude product was suspended in 100 mLs of ethyl ether, and the resulting yellow solid was collected by vacuum filtration to afford 14.1 g (66%) of a pale yellow solid: $^1$H NMR (400 MHz, DMSO-d$_6$) δ 8.97 (d, J=2.2 Hz, 1H), 8.53 (dd, J=4.8, 1.6 Hz, 1H), 8.12-8.03 (m, 1H), 7.45 (dd, J=7.9, 4.8 Hz, 1H), 6.99 (s, 1H), 6.28 (bs, 2H); $^{13}$C-NMR (101 MHz, CDCl$_3$) δ 151.72, 148.55, 146.06, 145.40, 131.57, 130.18, 129.93, 122.20.

Example 2

Preparation of 4-chloro-2-(pyridin-3-yl)-1,3-thiazol-5-amine hydrochloride

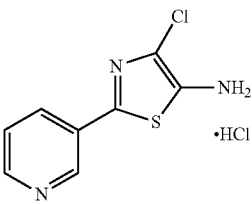 [SMILES: Nc1sc(-c2cccnc2)nc1Cl ; Cl]

To a dry 250 ml round bottom flask equipped with magnetic stirrer, was charged 6.3 g (35.5 mmoles) of 2-(pyridin-3-yl)-1,3-thiazol-5-amine, and 100 mLs of anhydrous 1,4-dioxane. The solution was cooled to ~0° C. and 4.75 g (35.5 mmoles) of N-chlorosuccinimide was added portionwise at a rate that maintained the temperature below 10° C. The reaction mixture was stirred at 5-10° C. for 20 minutes, and then filtered through a small pad of diatomaceous earth. The filtrate was diluted with 50 mLs of diethyl ether, and acidified with 10 mLs of 4.0 M HCl in 1,4-dioxane. The resulting solid was collected by vacuum filtration, washed with ethyl ether (100 mLs) and methylene chloride (500 mLs), and then dried in vacuuo at 40° C. to afford 7.5 g (85%) of an orange solid: $^1$H NMR (400 MHz, DMSO-d$_6$) δ 9.08 (d, J=2.1 Hz, 1H), 8.76 (dt, J=9.5, 4.7 Hz, 1H), 8.66 (ddd, J=8.3, 2.0, 1.3 Hz, 1H), 7.97 (dt, J=15.6, 7.8 Hz, 1H).

Example 3

Preparation of N-(4-chloro-2-(pyridin-3-yl)thiazol-5-yl)-2-methyl-3-(methylthio)propanamide

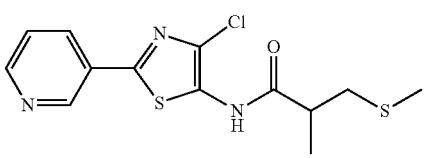 [SMILES: CSCC(C)C(=O)Nc1sc(-c2cccnc2)nc1Cl]

To a dry 500 ml round bottom flask equipped with magnetic stirrer, thermometer, addition funnel, and nitrogen inlet was charged 7.5 g (30.2 mmoles) of 4-chloro-2-(pyridine-3-yl)-1,3-thiazol-5-amine hydrochloride and 200 mLs of anhydrous methylene chloride. The resulting suspension was cooled to 15° C., and 5.98 g (76 mmoles) of pyridine was added at a rate that maintained the temperature below 20° C. 1.85 g (15.11 mmoles) of N,N-dimethylpyridin-4-amine was added in one portion and the resulting yellow solution was stirred at 5° C. for 10 minutes. A solution of 2-methyl-3-(methylthio)propanoyl chloride (5.54 g 36.3 mmoles) in 25 mLs of methylene chloride was added dropwise at a rate that maintained the temperature below 15° C. The reaction was stirred at ambient temperature for 12 hours, than poured into 200 mLs of water. The target was extracted with methylene chloride (3×100 mLs) and the combined methylene chloride extracts were washed with 0.5 N aqueous hydrochloric acid (100 mLs), water (100 mLs) and saturated aqueous sodium chloride solution (100 mLs). The organic extract was dried over anhydrous magnesium sulfate, filtered, and concentrated under vacuum on a rotary evaporator. The crude product was purified by silica gel flash chromatography, eluting with a gradient of 100% hexane to 100% ethyl acetate over 30 minutes to yield a yellow oil (5.4 g, 55%): $^1$H NMR (400 MHz, CDCl$_3$) δ 9.12 (dd, J=2.3, 0.8 Hz, 1H), 9.00 (s, 1H), 8.64 (dd, J=4.8, 1.6 Hz, 1H), 8.17 (ddd, J=8.0, 2.3, 1.6 Hz, 1H), 7.37 (ddd, J=8.0, 4.9, 0.8 Hz, 1H), 3.00-2.57 (m, 3H), 2.17 (s, 3H), 1.38 (d, J=6.7 Hz, 3H); $^{13}$C NMR (101 MHz, CDCl$_3$) δ 171.68, 155.24, 150.55, 146.75, 132.81, 129.26, 127.62, 124.99, 123.80, 40.85, 37.98, 17.46, 16.45.

Example 4

Preparation of N-(4-chloro-2-(pyridin-3-yl)thiazol-5-yl)-N,2-dimethyl-3-(methylthio)propanamide

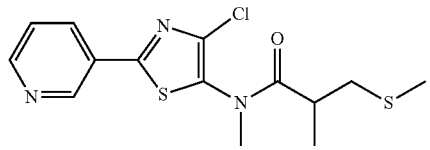 [SMILES: CSCC(C)C(=O)N(C)c1sc(-c2cccnc2)nc1Cl]

To a dry 50 ml round bottom flask equipped with magnetic stirrer, addition funnel, and nitrogen inlet was charged 1.0 g (3.05 mmoles) of N-(4-chloro-2-(pyridin-3-yl)-1,3-thiazol-5-yl)-2-methyl-3-(methylthio)propanamide and 10 mLs of anhydrous N,N-dimethyl formamide. To the resulting solution was then added 1.1 g (3.36 mmoles) of cesium carbonate powder in one portion, followed by the dropwise addition of 0.476 g (3.36 mmoles) of iodomethane in 5 mLs of anhydrous N,N-dimethylformamide. The heterogeneous mixture was stirred at ambient temperature for 12 hours, and then poured into 200 mLs of water and extracted with methylene chloride (3×100 mLs). The combined organic extracts were washed with water (100 mLs), saturated aqueous sodium chloride solution (100 mLs) dried over anhydrous magnesium sulfate, filtered, and concentrated under vacuum on a rotary evaporator. The crude product was purified by silica gel flash chromatography, eluting with a gradient of 100% hexane to 100% ethyl acetate over 20 minutes to yield a yellow oil (0.93 g, 89%): $^1$H NMR (400 MHz, CDCl$_3$) δ 9.12 (d, J=1.4 Hz, 1H), 8.73 (d, J=3.8 Hz, 1H), 8.34-8.09 (m, 1H), 7.43 (dd, J=7.9, 4.9 Hz, 1H), 3.30 (s, 3H), 3.06-2.70 (m, 2H), 2.49 (d, J=7.4 Hz, 1H), 2.04 (s, 3H), 1.21 (d, J=6.4 Hz, 3H); $^{13}$C NMR (101 MHz, DMSO-d$_6$) δ 175.22, 162.37, 151.91, 146.53, 136.46, 134.64, 133.35, 127.98, 124.27, 37.47, 36.71, 36.47, 17.56, 15.44.

Example 5

Preparation of N-(4-chloro-2-(pyridin-3-yl)thiazol-5-yl)-N-ethyl-2-methyl-3-(methylthio)propanamide

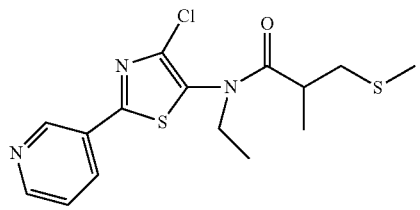 [SMILES: CCN(C(=O)C(C)CSC)c1sc(-c2cccnc2)nc1Cl]

To a dry 50 ml round bottom flask equipped with magnetic stirrer, addition funnel, and nitrogen inlet was charged 1.0 g (3.05 mmoles) of N-(4-chloro-2-(pyridin-3-yl)-1,3-thiazol-5-yl)-2-methyl-3-(methylthio)propanamide and 10 mLs of anhydrous N,N-dimethyl formamide. To the resulting solution was then added 1.1 g (3.36 mmoles) of cesium carbonate powder in one portion, followed by the dropwise addition of 0.523 g (3.36 mmoles) of iodoethane in 5 mLs of anhydrous N,N-dimethyl formamide. The heterogeneous mixture was stirred at ambient temperature for 12 hours. Analysis of an aliquot indicated incomplete reaction. An additional 100 ul of iodoethane was added and the reaction was heated at 60° C. for 3 hours, then poured into 200 mLs of water and extracted with methylene chloride (3×100 mLs). The combined organic extracts were washed with water (100 mLs), saturated aqueous sodium chloride solution (100 mLs) dried over anhydrous magnesium sulfate, filtered, and concentrated under vacuum on a rotary evaporator. The crude product was purified by silica gel flash chromatography, eluting with a gradient of 100% hexane to 100% ethyl acetate over 20 minutes to yield a yellow oil which crystallized upon standing (0.38 g, 35%): mp 80-81° C.; $^1$H NMR (400 MHz, CDCl$_3$) δ 9.12 (d, J=1.9 Hz, 1H), 8.72 (dd, J=4.8, 1.4 Hz, 1H), 8.22 (ddd, J=8.0, 2.2, 1.8 Hz, 1H), 7.43 (ddd, J=8.0, 4.8, 0.6 Hz, 1H), 4.03-3.80 (m, 1H), 3.80-3.59 (m, 1H), 2.97-2.68 (m, 2H), 2.60-2.39 (m, 1H), 2.03 (s, 3H), 1.30-1.16 (m, 6H); $^{13}$C NMR (101 MHz, DMSO-d$_6$) δ 175.66, 162.63, 151.89, 147.14, 138.19, 133.49 133.23, 128.58, 123.90, 44.81, 38.94, 37.93, 18.16, 16.83, 12.90.

What is claimed is:
1. A process comprising

Scheme One

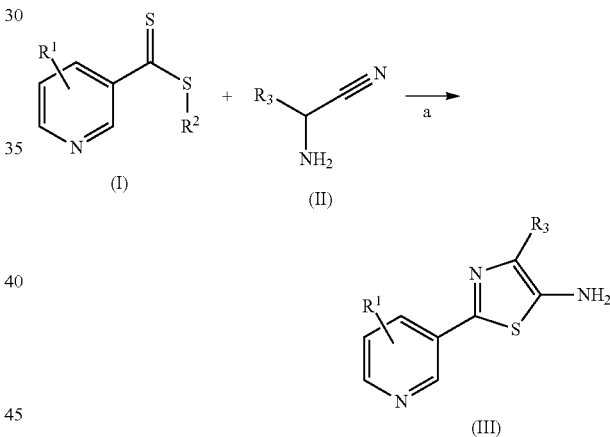

(i) cyclizing compound (I) with compound (II) to produce compound (III);
wherein
(A) each $R^1$ is H, alkyl;
(B) $R^2$ is unsubstituted $(C_1-C_6)$alkyl; and
(C) $R^3$ is H
wherein step a is conducted in a polar protic solvent.

2. A process according to claim 1 wherein step a said polar protic solvent is selected from the group consisting of n-butanol, isopropanol, n-propanol, ethanol, methanol, acetic acid, water, or a mixture thereof.

3. A process according to claim 2 wherein said polar protic solvent is methanol.

4. A process according to claims 1, 2, or 3, said process further comprising halogenating said $R^3$ to F, Cl, Br, or I wherein said halogenating is conducted in a polar solvent and said halogenating is conducted at a temperature from 0° C. to ambient.

5. A process according to claim 4 wherein said halogenating is conducted in a polar solvent selected from the group consisting of dichloromethane, tetrahydrofuran, ethyl acetate, acetone, dimethylformamide, acetonitrile, and dimethyl sulfoxide.

6. A process according to claim 5 wherein said solvent is dichloromethane.

7. A process according to claim 6 wherein $R^3$ is Cl.

8. A process according to claim 1 wherein $R^2$ is methyl.

* * * * *